(12) United States Patent
Wantink et al.

(10) Patent No.: US 7,678,075 B2
(45) Date of Patent: Mar. 16, 2010

(54) INFUSION CATHETER AND USE THEREOF

(75) Inventors: Ken Wantink, Temecula, CA (US); William E. Webler, Escondido, CA (US); Jeong Lee, Diamond Bar, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1311 days.

(21) Appl. No.: 11/028,350

(22) Filed: Dec. 30, 2004

(65) Prior Publication Data

US 2006/0149186 A1    Jul. 6, 2006

(51) Int. Cl.
*A61M 29/00*    (2006.01)

(52) U.S. Cl. .................................................. 604/96.01
(58) Field of Classification Search .............. 604/96.01, 604/97.01
See application file for complete search history.

(56) References Cited

U.S. PATENT DOCUMENTS

| | | | | |
|---|---|---|---|---|
| 4,299,226 | A | | 11/1981 | Banka |
| 4,988,356 | A | * | 1/1991 | Crittenden et al. .......... 606/192 |
| 4,994,033 | A | | 2/1991 | Shockey et al. |
| 5,318,532 | A | * | 6/1994 | Frassica ................... 604/97.01 |
| 5,368,567 | A | | 11/1994 | Lee |
| 5,415,637 | A | | 5/1995 | Khosravi |
| 5,470,322 | A | | 11/1995 | Horzewski et al. |
| 5,527,292 | A | * | 6/1996 | Adams et al. ................ 604/171 |
| 5,704,908 | A | * | 1/1998 | Hofmann et al. .............. 604/21 |
| 5,807,318 | A | | 9/1998 | St. Goar et al. |
| 5,840,066 | A | | 11/1998 | Matsuda et al. |
| 5,879,499 | A | * | 3/1999 | Corvi .......................... 156/175 |
| 5,951,513 | A | * | 9/1999 | Miraki ..................... 604/96.01 |
| 6,027,475 | A | | 2/2000 | Sirhan et al. |
| 6,056,721 | A | | 5/2000 | Shulze |
| 6,063,056 | A | * | 5/2000 | Engelberg ................ 604/97.01 |
| 6,117,105 | A | * | 9/2000 | Bresnaham et al. ...... 604/96.01 |
| 6,186,978 | B1 | | 2/2001 | Samson et al. |
| 6,234,995 | B1 | * | 5/2001 | Peacock, III ............. 604/96.01 |
| 6,306,151 | B1 | * | 10/2001 | Lary .......................... 606/159 |
| 6,626,885 | B2 | | 9/2003 | Massengale |

(Continued)

OTHER PUBLICATIONS

PCT Partial Search Results dated Apr. 18, 2006 of PCT/US2005/045629, filed Dec. 16, 2005.

*Primary Examiner*—Nicholas D Lucchesi
*Assistant Examiner*—Aarti B Berdichevsky
(74) *Attorney, Agent, or Firm*—Blakely Sokoloff Taylor & Zafman LLP

(57) ABSTRACT

An infusion catheter having a distal shaft with an infusion tube extending from a proximal end to a distal end of the distal shaft, and a proximal cannula with an inner dimension and a distal end attached to a proximal end of the distal shaft to define an opening between the inner diameter of the infusion tube and the inner dimension of the proximal cannula. Also, a guidewire tube disposed within the inner dimension and the distal shaft and extending from the proximal end of the proximal cannula to the distal end of the distal shaft. The inner diameter of the infusion tube, the opening, the exterior dimension of the guidewire tube and the inner dimension cooperate and define sufficient cross sectional sizes to allow a treatment agent to be infused between the proximal end of the proximal cannula and the region of interest.

18 Claims, 4 Drawing Sheets

U.S. PATENT DOCUMENTS

| | | | |
|---|---|---|---|
| 6,645,135 B1 * | 11/2003 | Bhat | 600/3 |
| 6,764,461 B2 | 7/2004 | Mickley et al. | |
| 7,131,963 B1 * | 11/2006 | Hyde | 604/96.01 |
| 7,238,168 B2 * | 7/2007 | Sirhan et al. | 604/96.01 |
| 7,384,411 B1 * | 6/2008 | Condado | 604/96.01 |
| 2001/0001812 A1 * | 5/2001 | Valley et al. | 604/96.01 |
| 2002/0091354 A1 * | 7/2002 | Navia et al. | 604/96.01 |
| 2002/0091407 A1 * | 7/2002 | Zadno-Azizi et al. | 606/200 |
| 2003/0014008 A1 | 1/2003 | Jacques | |
| 2003/0105427 A1 | 6/2003 | Lee et al. | |

* cited by examiner

INFUSION CATHETER AND USE THEREOF

BACKGROUND

1. Field

Cardiovascular infusion catheters.

2. Background

It is increasingly important that a physician or surgeon delivering substances, such as a treatment agent or drug, is able to efficiently and accurately locate the desired target tissue for effective delivery of the substance. This is particularly true when the concentration of the substance required at the target site cannot be safely or effectively achieved by introduction of the substance to a location remote from the target site. Moreover, the physician may only want to treat the diseased portion of an organ or tissue and avoid treating any healthy portions.

Such localized treatment is desired not only for substance delivery but is necessary for other treatments, such as myocardial revascularization. Myocardial revascularization is a procedure in which "holes" are formed in ischemic ventricular tissue to increase blood flow to the treated area. It is thought that the tissue damage (e.g., holes) encourages growth of blood vessels in the treated area. Thus, similar to substance delivery, myocardial revascularization is a procedure that is preferably performed only on specific areas that require treatment.

For example, to achieve localized treatment of tissue, such as tissue in a heart, physicians and surgeons can use catheters and occlusion devices. Specifically, cardiovascular guide catheters are generally percutaneous devices used to advance through a vasculature of a patient to a region of interest and are devices through which another catheter or device may be inserted. Infusion or delivery catheters are generally catheters used to deliver or infuse a treatment agent to a region of interest in a vasculature of a patient and typically may be inserted through another catheter (e.g., a guide catheter). Moreover, occlusion devices, such as balloons, may be attached to a guide catheter or infusion catheter to occlude a region of interest in a vasculature. Guidewires are generally devices used to guide catheters through a vasculature of a patient to a region of interest and typically may be inserted through another catheter (e.g., an introducer and/or a guide catheter).

SUMMARY

There is disclosed an infusion catheter or cannula for infusing a treatment agent to a region of interest of a blood vessel (e.g., such as an artery or vein, including of the human heart). The infusion catheter may have a balloon attached to its outer surface near its distal end to occlude the blood vessel from allowing treatment agent infused proximal or distal to the balloon from being perfused away from the region of interest. Example balloons are made of a material and with a dimension to have an outer diameter that may be inflated to occlude a blood vessel.

Specifically, an infusion catheter may have a distal shaft with an infusion tube extending from a proximal end to a distal end of the distal shaft, and a proximal cannula with an inner dimension and a distal end attached to a proximal end of the distal shaft to define an opening between the inner diameter of the infusion tube and the inner dimension of the proximal cannula. The catheter may also have a guidewire tube disposed within the inner dimension and the distal shaft and extending from the proximal end of the proximal cannula to the distal end of the distal shaft. The inner diameter of the infusion tube, the opening, the exterior dimension of the guidewire tube and the inner dimension cooperate and define sufficient cross sectional area to allow a treatment agent to be infused from the proximal end of the proximal cannula, distally into the infusion tube and out into the region of interest. The infusion inner dimension may exist over most of the length of the catheter before transitioning to the more restrictive infusion tube, which only exists in the shorter distal shaft. The shorter distal shaft provides a portion of the catheter with a further reduced outer diameter for easier guiding and to access smaller diameter blood vessels. Optionally, the infusion catheter may have a support mandrel extending longitudinally partially or completely therethrough.

A process for making or manufacturing the infusion catheter may include placing a guidewire tube, an inflation tube, and an infusion tube within a shorter length of an outer layer of Pebax® and/or nylon (and optionally an inner layer of adhesive polymer). The outer layer and tubes may then be disposed within a shrink tube to form an assembly. The assembly is heated to shrink the shrink tube, and to fuse or bond the tubes and outer layer. Mandrels may be disposed within into the guidewire tube, the inflation tube, and the infusion tube before heating. The portion of the infusion tube extending past the shorter length outer layer is removed, or is excluded during making. The guidewire tube and the inflation tube are disposed into a larger diameter proximal cannula such that an opening is formed between the infusion tube and the inner dimension of the proximal cannula. A length of the inner surface of the outer layer is attached to a length of the outer surface of the proximal cannula, such as by adhesive, heat bonding, or laser bonding.

A three-way side arm adapter may be attached to the proximal end of the proximal cannula having a guidewire, inflation, and infusion openings to access the guidewire tube, inflation tube, and infusion inner dimension. Also, an infusion lumen may be formed between the infusion opening and the inner dimension by infusing adhesive around a mandrel inserted between the infusion opening in the adapter and the inner dimension. The mandrels are removed from the guidewire tube, the inflation tube, the infusion tube, and the infusion lumen to form the device.

Moreover, the infusion catheter may have a guidewire lumen (e.g., through the guidewire tube) through which to extend a guidewire, such as for "over-the-wire" guiding of the infusion catheter. Since the infusion catheter has a smaller outer diameter than other designs, it is able to maximize infusion flow with no separate inner tube defining the proximal portion of the infusion lumen, while being flexible, and having a low profile. In other words the infusion catheter can be built with a smaller outer diameter to (1) increase the ability to introduce and withdraw a guidewire within a lumen of the cannula, (2) increase the ability to inject fluoroscopic agent, (3) increase the ability to inflate the balloon at the distal portion of the catheter, (4) use a smaller required outer diameter introducer/guide catheter, and (5) result in fewer insertion site complications. Thus, the infusion catheter may be more successfully guided to a region of interest in a blood vessel to provide treatment agent to that region.

BRIEF DESCRIPTION OF THE DRAWINGS

Various features, aspects and advantages will become more thoroughly apparent from the following detailed description, the set of claims, and accompanying drawings in which:

DETAILED DESCRIPTION

Figure 1:
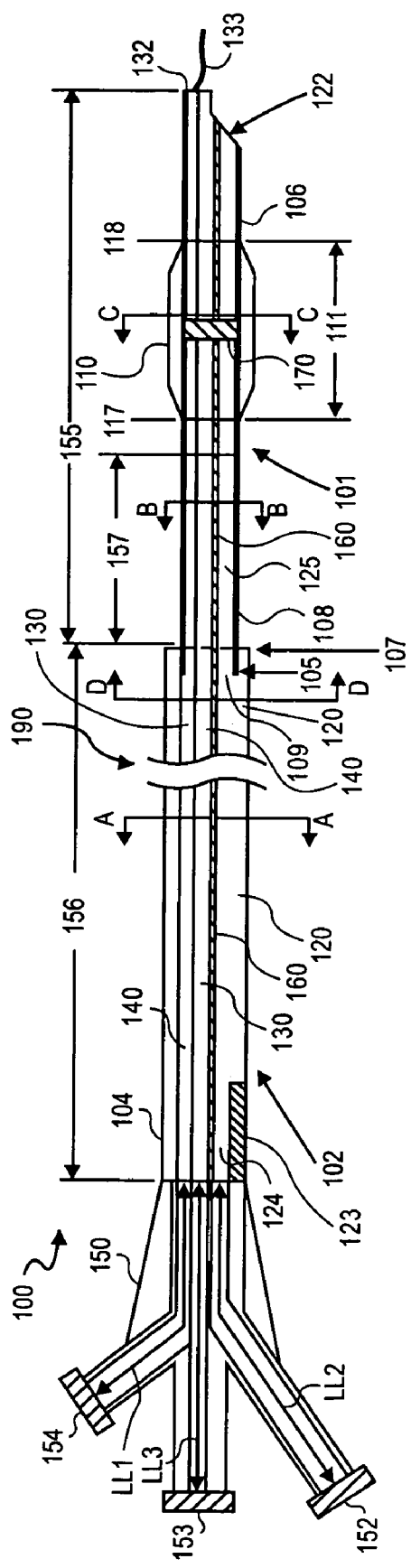
FIG. 1 illustrates an apparatus for infusing a treatment agent to a region of interest in a blood vessel.

According to embodiments, a balloon can be used with a cannula or catheter that has a dimension suitable for percutaneous advancement through a blood vessel to infuse a treatment agent (e.g., such as biological agents) into a region of interest, such as arterial vessels and/or venous vessels. For example, FIG. 1 illustrates an apparatus for infusing a treatment agent to a region of interest in a blood vessel. FIG. 1 shows apparatus 100 having distal shaft 101 having a length 155, and infusion tube 125 extending from proximal end 105 to distal end 106 of distal shaft 101. FIG. 1 also shows proximal cannula 102 having length 156 and inner dimension 120 between distal end 107 and proximal end 104 of proximal cannula 102. Distal end 107 of proximal cannula 102 is attached to proximal end 105 of distal shaft 101 at a "junction" so that opening 109 is formed between the inner diameter (e.g., lumen) of infusion tube 125 and inner dimension 120 of proximal cannula 102.

Length 156 may be a length between 50 centimeters and 200 centimeters, such as by being a length of 50 centimeters, 75 centimeters, 90 centimeters, 100 centimeters, 110 centimeters, 112 centimeters, 114 centimeters, 116 centimeters, 120 centimeters, 130 centimeters, 135 centimeters, 150 centimeters, 175 centimeters, or 200 centimeters. Also, length 155 may be a length between 10 centimeters and 60 centimeters, such as by being a length of 10 centimeters, 15 centimeters, 20 centimeters, 25 centimeters, 28 centimeters, 30 centimeters, 32 centimeters, 35 centimeters, 40 centimeters, 45 centimeters, 50 centimeters, or 60 centimeters. In some embodiments, length 156 and length 155 may correspond to appropriate lengths for extending apparatus 100 from a femoral artery, or through a vein through blood vessels and to the heart of a human being.

FIG. 1 shows outer surface of distal shaft 101 at or adjacent proximal end 105 under and attached to the inner surface of proximal cannula 102 at or near distal end 107. Distal shaft 101 may be adhered to or attached to proximal cannula 102 by adhesive, heat bonding, or laser bonding. It can be appreciated that herein, "heat bonding" may include bonding by a heat shrink process; by a process including a heat shrink tube; and/or by a process including an adhesive, a light, and/or a laser. Proximal cannula 102 may be described as a proximal shaft section having an outer tubular member defining a proximal portion of an infusion path (e.g., a path including inner dimension 120 and infusion tube 125).

In some embodiment, distal shaft 101 has a radially expandable member, such as an occlusion device, a balloon or a filter, on a distal end of the shaft. For instance, FIG. 1 shows shaft 101 having balloon 110 axially connected to distal shaft 101 at balloon section 111 or adjacent distal end 106. Balloon 110 may be a high compliance balloon. For example, balloon 110 may be a balloon including a property such that when inflated to a selected inflation volume the balloon will expand in size to an outer diameter sufficient to occlude a blood vessel as described herein. In one example, balloon 110 may be a high-compliance balloon made of a low durometer material. More particularly, balloon 110 may be designed by a process and/or of the materials described herein to have an outer diameter that can be controlled by controlling the amount of inflation volume of a liquid (e.g., such as water, saline solution, or a fluid having a fluoroscopy contrast agent) used to inflate the balloon. Moreover, according to embodiments balloon 110 may have a property such that when inflated to a plurality of increasing inflation volumes, the balloon forms a plurality of increasing radial outer diameters, and has an inflation pressure that increases by less than five percent in pressure over the range of the increasing inflation volumes. Such a balloon may be used as an occlusion device.

It is also considered that balloon 110 may be designed by a process and/or of the materials described herein and may have a dimension, characteristic, deflated outer diameter, and/or deflated length, such that the outer diameter of the balloon may be inflation pressure controlled. More particularly, a balloon may be designed by a process and/or of the materials described herein to have an outer diameter that can be controlled by controlling the amount of inflation pressure of a liquid (e.g., such as water, saline solution, or a fluid having a fluoroscopy contrast agent) used to inflate the balloon. Again, such a balloon may be used as an occlusion device.

According to embodiments, balloon 110, may be heat bonded, laser bonded, bonded using a heat shrink process, or attached with an adhesive to distal shaft 101. Specifically, balloon 110 may be bonded using a heat shrink process that includes one or more pieces of shrink tube around the proximal and distal ends of the balloon to bond the balloon to balloon section 111 of distal shaft 101 so that the balloon exterior surface inflates to symmetrical shape with respect to an axis of the cannula. For instance, bonded using a heat shrink process may provide and even and straight bond of a balloon tube to a cannula with respect to an axis of the cannula to effect such symmetrical inflation of the balloon over a range of inflation pressures and/or volumes as mentioned herein.

Balloon 110 may be blow-molded, have "wings" folded around the balloon in the uninflated configuration, or be "wingless". Balloon 110 may be an occlusion balloon, a low compliance balloon, and/or a high compliance balloon. Additionally balloon 110 may function as an anchoring balloon fixing distal end 106 at or near a position (e.g., a region of interest) in a blood vessel. In some embodiments, instead of balloon 110, another radially expandable member, such as a filter may be used on the distal end of the distal shaft.

Moreover, FIG. 1 shows marker band 170, such as a radio-opaque marker like a material or polymer including a tungsten or a barium compound. Marker band 170, may be a material formed or shaped using a heat shrink process, an extruded material, a fused material, a mechanically constrained material, a laser-bonded material, a heat-bonded material, or other material around, in, or under exterior surface 108 of distal shaft 101. For instance marker band 170 may be a length of an extruded tube of plastic and tungsten placed or slid onto surface 108 of a material forming distal shaft 101. Alternatively, marker band 170 may be placed or slid directly around guidewire tube 130, infusion tube 125, optionally inflation tube 140, and optionally mandrel 160, without another material forming distal shaft 101. In some cases, marker band 170 may be formed on or over a material forming distal shaft 101, guidewire tube 130, infusion tube 125, inflation tube 140 (optionally), and/or mandrel 160 (optionally) using a heat shrink process known in the art and/or described below for block 730. For instance, marker band 170 may be a material put in place using a heat shrink process to form or shape the marker on or over the surface of the distal shaft by heating a heat shrink tube disposed around band 170 to shrink the heat shrink tube and bond, "melt", or fuse the material of band 170 to the material below. Moreover, marker band 170 may assist in or be used to retaining together guidewire tube 130, infusion tube 125, optionally inflation tube 140, and optionally mandrel 160 within balloon section 111 of distal shaft 101. In this sense it may be part of the melted/formed plastic that holds the tubes together. In some cases, band 170 may be formed of a radio-opaque marker ring attached to or constrained on guidewire tube 130, infusion tube 125, optionally inflation tube 140, and/or optionally mandrel 160 (such as on exterior surface 108 at balloon section 111) by crimping, an adhesive, by formed fillets or other means.

Additionally, FIG. 1 shows guidewire tube 130, which has an inner dimension and is made of a material suitable to receive guidewire 133 to guide distal end 106 of distal shaft 101 through a blood vessel, such as a blood vessel of a human being. Guidewire 133 may be between 0.018" and 0.014" in diameter and the inner dimension (conventionally termed the inner diameter or "ID") of cannula 130 will typically be 0.002" to 0.004" larger in diameter than the guidewire. Thus, the size of the guidewire will be almost as large as the ID of the cannula. Guidewire 133 may be stiff enough to be straight or form a gentle curves in response to gravity. Guidewire 133 may also have a rounded, more flexible, atraumatic distal tip. The tip of the guidewire may be straight or pre-formed with a small curve or bend.

Specifically, guidewire tube 130 is suitable to guide distal end 106 to a region of interest in a blood vessel, such as an artery, or vein (e.g., including the arteries and veins of a human heart) in an "over-the-wire" fashion using guidewire 133 extending through guidewire tube 130 and exiting proximal end 104 and distal end 106. For example, guidewire tube 130 may be adapted to receive a guidewire and/or have a guidewire disposed therein and exiting distal end 106 at guidewire opening 132, so that apparatus 100 can be used in an over-the-wire fashion, and/or have the guidewire removed therefrom.

It should be noted that the design of apparatus 100 or guidewire tube 130 is not limited to an over-the-wire configuration. For example, the guidewire cannula could be cut off (e.g., at proximal end 105 of distal shaft 101, the same as the infusion tube) and then have its proximal end blocked (i.e. by an adhesive, an adhesive and a plug, a miscible polymer plug or an adhesive polymer coated plug, prior to the heat shrink process). Then an access hole can be cut into the guidewire lumen just distal to the plug (commonly called the "RX notch"). In this configuration, the guidewire only engages the distal end of apparatus 100 and is in an "Rapid eXchange" (RX) configuration.

Referring to FIG. 1, guidewire tube 130 may have a guidewire proximal port located distal to proximal end 104 such that apparatus 100 can be used in rapid exchange fashion. Typically, such a guidewire proximal port is located a substantial distance from proximal end 104, such as, in one embodiment, between about 10 cm to about 35 cm from guidewire opening 132 at distal end 106. It is considered that guidewire tube 130 may have a proximal opening located proximal to balloon 110 and within 35 centimeters of distal end 106.

Embodiments include an access system (introducer and/or guide catheter) where no infusion catheter engagement (e.g., apparatus 100) with a guidewire is required. In this case, apparatus 100 may be designed as specified above for the RX configuration, except that the guidewire tube (e.g., tube 130), the plug and the RX notch could be omitted entirely. Thus, apparatus 100 can be delivered or placed in a blood vessel without a guidewire or engagement features therefore.

For example, the proximal portion of a target vasculature (e.g., a region of interest, such as an ostium, vessel branch or sinus) can be accessed with an access guide catheter to sub-select a proximal portion of the target vasculature. The access guide catheter can essentially be the same as a normal guide catheter (e.g., guide catheter as described herein) and be used to access the proximal vasculature in a conventional manner. A "rail" catheter may then be tracked into the access guide catheter to place the rail catheter more distally into the accessed target vasculature and/or to sub-select more distal vessel branches at or across the regions of interest in the target vasculature.

The access guide catheter is then removed over the rail catheter, leaving the rail catheter in place at or across the region of interest in the target vasculature. A delivery catheter is tracked over the rail catheter. The delivery catheter is similar in design to the access guide catheter, except it includes a more flexible section added to its distal end. This more flexible section of the delivery catheter is positioned over the rail catheter to reside across the target vasculature's (or other vascular structures) regions of interest.

The rail catheter may be constructed with variable flexibility. In one embodiment, the rail catheter is much longer (e.g., twice as long) than the access guide catheter or delivery catheter to assure that portions of the rail catheter will be accessible to the physician to hold in place while the access guide catheter is withdrawn or the delivery catheter is inserted over the rail catheter. The rail catheter may accommodate a guidewire in its inner diameter and/or include a shaped distal end for easy maneuvering and sub-selection of the target vasculature.

Also, the rail catheter may include an access port that is detachable (e.g., a detachable Luer, rotating hemostatic valve or other similar component) to allow the access guide catheter to be removed over the rail catheter and the delivery catheter to be disposed over the rail catheter without the access guide catheter or the delivery catheter having a very large inner diameter. For example, the proximal end of the rail catheter can be configured to include a male or female screw tip that is complimentary with a respective male or female screw receptor on the distal tip on the access port. The access port is detached to allow the access guide catheter to be withdrawn over the rail catheter once the rail catheter is in place. Additionally, the detachable access port can be detached to allow the delivery catheter to be tracked over the rail catheter. The outer diameter of the rail catheter and the inner diameter of the delivery catheter could be substantially close to each other so they can move relatively easy with respect to each other without too much excess space between the outer diameter of the rail catheter and the inner diameter of the delivery catheter.

The rail catheter is then withdrawn and removed. Apparatus 100 is then inserted into the delivery catheter and positioned at a desired location within the target vasculature and within the flexible section of the delivery catheter. The delivery catheter may then be withdrawn over surface 108 of apparatus 100 to expose the desired portions of apparatus 100 (e.g., such as balloon 110) to or at the target vasculature.

Also, apparatus 100 may be part of a catheter kit also having a guide catheter with an occlusion device at the distal end of the guide catheter. The infusion catheter may be guided to a location in a blood vessel within an interior space of the guide catheter. The infusion catheter can then be extended beyond the distal end of the guide catheter and to a region of interest in a blood vessel to provide treatment agent to that region. While apparatus 100 is within the guide catheter, inner dimension 120 is sufficient to allow a volume of a volume of one of a fluoroscopy contrast agent, a fluoroscopy contrast media, a fluoroscopy contrast liquid to be infused into the blood vessel proximal of the balloon to view a portion of the volume of contrast adjacent to the balloon to determine whether the blood vessel is occluded at the balloon.

FIG. 1 also shows inflation tube 140 disposed within inner dimension 120 of distal shaft 101 and extending from proximal end 104 to balloon 110. Balloon 110 is shown attached to exterior surface 108 of distal shaft 101 at or near distal end 106. Inflation tube 140 has an inner dimension and is made of a material suitable to receive a volume of fluid at proximal end 104 and cause a volume of fluid to inflate balloon 110. In addition, inflation tube 140 may be coupled to an inflation device or syringe to inflate balloon 110 (e.g., such as via adapter 150 mentioned below).

As shown in FIG. 1, break 190 separates proximal end 104 and distal end 107 of proximal cannula 102. It can be noted that the positions of guidewire tube 130 and inflation tube 140 are switched at break 190. For instance, break 190 may represent a length of proximal cannula 102, similar to that at perspective A (e.g., see FIG. 2) where guidewire tube 130 and inflation tube 140 "cross over" or where cannula 102 is rotated, flexed, bent or otherwise provides for the orientation of guidewire tube 130 and inflation tube 140 as show distally to break 190. Alternatively, embodiments include cannula 102 distal to break 190 and/or distal shaft 101 having guidewire tube 130 and inflation tube 140 in opposite positions shown with respect to each other (e.g., in switched positions) in FIG. 1.

It can be appreciated that cannulas and tubes described herein, such as proximal cannula 102, infusion tube 125, guidewire tube 130, and inflation tube 140 have a lumen therethrough, such as a lumen defining an inner diameter within the cannula or tube. Also, inner dimension 120 may be described as the volume or space within proximal cannula 102 (e.g., such as the volume or space within an inner diameter of wall 202) less the volume or space taken up by other features or devices within that volume or space. Specifically, inner dimension 120 may be defined as the volume or space within proximal cannula 102 less the volume or space defined and occupied by guidewire tube 130, inflation tube 140, and/or mandrel 160. Also, inner dimension 120 may consider the cross-sectional area of inner dimension 120 at points along the length between proximal end 104 and distal end 107 of proximal cannula 102.

FIG. 1 also shows adapter 150 (e.g., such as a "hub", a three arm adapter, or a three-way side arm) attached to proximal end 104 of proximal cannula 102. Adapter 150 may be attached to proximal end 104 using adhesive, heat bonding, or laser bonding. Adapter 150 includes guidewire opening 153 having an inner diameter communicating with the lumen of guidewire tube 130. For instance, guidewire opening 153 may receive guidewire 133 to be extended through guidewire tube 130. Guidewire 133 may exit opening 153, such as in an over-the-wire configuration. FIG. 1 shows guidewire opening 153 as the center arm of the adapter to avoid bending or rubbing of a guidewire on the inner diameter of the adapter (e.g., causing difficulty in positioning apparatus 100 and/or moving apparatus 100 relative to the guidewire). Embodiments where guidewire opening 153 is not the center arm of the adapter are also considered.

Adapter 150 also has inflation opening 154 having an inner diameter communicating with the lumen of inflation tube 140. For instance, inflation opening 154 may have a dimension suitable for receiving a volume of fluid to cause an inflation volume of fluid to be pushed into balloon 110 attached to exterior surface 108 where the volume of inflation fluid is equal to a volume of fluid to inflate balloon 110 to occlude a blood vessel. Thus, the inner dimension of tube 140 may communicate fluid with an inflation and deflation device attached or coupled to opening 154 such that the inflation device may inflate and deflate balloon 110.

Likewise, adapter 150 includes infusion opening 152 having an inner diameter communicating with inner dimension 120. For instance, infusion opening 152 may have infusion lumen 124 extending from opening 152 past proximal end 104 and into inner dimension 120. Infusion opening 152 and infusion lumen 124 allow treatment agent to be infused from infusion opening 152 into inner dimension 120, so that treatment agent may be infused between proximal end 104 and distal end 106 as described above. Opening 153 may be a port or opening to connect to a hemastatic valve. Opening 152 may port or opening having a spring loaded pressure seal. Also, opening 154 may port or opening to have an inflation device or syringe attached thereto.

Infusion lumen 124 may be formed by injection molding, casting, or infusing adhesive or epoxy 123 into infusion opening 152 and around a mandrel extending through infusion opening 152 and into inner dimension 120. The adhesive or epoxy may then be allowed to dry and the mandrel removed or pulled out through opening 152. Similarly, adapter 150 may be formed by injection molding, molded plastic, casting, cast metal, hardened adhesive, or hardened resin. Infusion lumen 124 may be formed of hardened adhesive, hardened resin, or molded plastic.

In embodiments, the outer surfaces of inflation tube 140 and infusion tube 125 may be spaced apart and separated by guidewire tube 130 along at least a section of distal shaft 101. Also, inflation tube 140 and guidewire tube 130 may extend side-by-side along the length of proximal cannula 102 (e.g., a proximal shaft section formed by an outer tubular member, such as surface 108). Next, distal shaft 101 may have a higher flexibility than proximal cannula 102. Finally, inflation tube opening 109 may be radially aligned with the inner diameter opening at distal end 107 of proximal cannula 102 (e.g., formed within surface 108).

In addition, as shown in FIG. 1, guidewire tube 130 may extend length LL3 in distance beyond or out of proximal end 104 to opening 153 as the same tube disposed within proximal cannula 102 or by attaching to a separate tube or lumen of adapter 150. Similarly, infusion lumen 124 may extend length LL2 in distance beyond or out of proximal end 104 to opening 152 as the same tube disposed within proximal cannula 102 or by attaching to a separate tube or lumen of adapter 150. Next, inflation tube 140 may extend length LL1 in distance beyond or out of proximal end 104 to opening 154 as the same tube disposed within proximal cannula 102 or by attaching to a separate tube or lumen of adapter 150. Length LL1, length LL2, and/or length LL3 may be equal or different distances in length. Also, it is to be appreciated that infusion tube 125, inner dimension 120 and lumen 124 may be of a dimension (e.g., considering cross-sectional area at points along the length between proximal end 104 and distal end 106) suitable to infuse a volume of treatment agent to a region of interest of a blood vessel and to aspirate a volume of blood and/or treatment agent from the region of interest. Similarly, inflation tube 140 may have a dimension suitable to inflate balloon 110 with a volume of a gas and/or liquid to a suitable inflation pressure (e.g., within a suitable timeframe, such as less than 20 seconds) and to maintain the inflation volume and/or inflation pressure for at least 3 minutes. Inflation lumen 140 and opening 154 may have a dimension suitable for deflating balloon 110 within a suitable timeframe (i.e. less than 20 seconds).

Guidewire tube 130, lumen 124, and/or inflation tube 140 may extend into or through adapter 150 or be attached to adapter 150 at proximal end 104. Thus, adapter 150 may include the proximal end of guidewire tube 130, the proximal end of inflation tube 140, and/or the proximal end of lumen 124.

In the RX configuration, adapter 150 doesn't require opening 153. Thus, in the RX configuration, adapter 150 may be replaced by a two arm adapter that does not include opening 153 or the lumen connecting opening 153 to proximal cannula 102. Also, in this configuration, guidewire tube 130 may be excluded from proximal cannula 102, and/or portions of distal shaft 101. As shown in FIG. 1, this configuration may include support mandrel 160 extended proximally into and anchored within proximal cannula 102, adapter 150, and/or distal shaft 101 to provide support to proximal portions of cannula 102 and/or apparatus 100 that will not be supported by a guidewire during catheter insertion and positioning using the RX configuration.

According to embodiments, apparatus 100 may be a cannula or catheter such as a delivery, infusion, inflation, and/or guide catheter or cannula. For instance, apparatus 100, cannulas, tubes, adapters, and balloons thereof may include materials, such as one or more of a synthetic or natural latex or rubber, such as a polymer material; a polyetheramide; a thermoplastic; a plasticiser free thermoplastic elastomer; a thermoplastic blend; a block copolymer of polyether and polyester; a biocompatible polymer such as a polyether block amide resin; a polycarbonate or acrylonitrile bubadiene styrene (ABS); a biocompatible polymer such as a polyether block amide resin; a styrene isoprene styrene (SIS), a styrene butadiene styrene (SBS), a styrene ethylene butylene styrene (SEBS), a polyetherurethane, an ethyl propylene, an ethylene vinyl acetate (EVA), an ethylene methacrylic acid, an ethylene methyl acrylate, an ethylene methyl acrylate acrylic acid, a polyetheretherketone (PEEK), a plastic, a polymer, a resin, a "Teflon"® (Teflon® is commercially available from DuPont Dow Elastomers of Wilmington, Del.), an adhesive polymer (e.g., such as "Primacore", Primacore® is commercially available from Dow Chemical Company of Midland, Mich.), a polyethylene (e.g., such as a low density polyethylene (LDPE), a mid-density polyethylene (MDPE), or a high density polyethylene (HDPE)), a heat-shrunk tube or tubing (e.g., such as polyester, high density polyethylene (HDPE) or fluorinated ethylene-propylene (FEP)), "Pebax", Pebax® is commercially available from Autochem Corporation of Puteaux, France), a block copolymer, a polycarbonate, a biocompatible polymer, styrene, a urethane, an acetate, an acid, an acrylate, a material from a material family of one of styrenic block copolymers and polyurethanes, a melt processible polymer, a low durometer material, a Pebax and nylon blend, and/or a nylon.

More particularly apparatus 100 may have a dimension and/or profile compatible with or suitable to be received within, and/or be slidably disposed within a guide catheter having an outer diameter in a range of between 3 French and 12 French, such as 3 French, 5 French, 6 French, 7 French, 8 French, 10 French, or 12 French. It is also contemplated that apparatus 100 may have a dimension suitable for percutaneous advancement through a blood vessel to infuse a treatment agent (e.g., such as biological agents) into a region of interest, such as arterial vessels and/or venous vessels.

In addition, infusion tube 125, opening 109, the exterior dimension of guidewire tube 130, and inner dimension 120 have crossed sections or cross-sectional areas and cooperate to allow a treatment agent to be infused from proximal end 104 through inner dimension 120 (e.g., such as around the outer dimension of guidewire tube 130 and inflation tube 140), through opening 109 and infusion tube 125, and out infusion opening 122 at distal end 106. Thus, a treatment agent such as media, bone marrow, stem cells, treatment fluid, or contrast may be infused between proximal end 104 and distal end 106 of apparatus 100.

Moreover, apparatus 100 may be designed and/or manufactured to have allow for a cannula or infusion catheter (e.g., by considering and/or selecting specific materials, inflation volumes, lengths, diameters, material thickness, etc. of distal shaft 101, proximal cannula 102, infusion tube 125, guidewire tube 130, inflation tube 140, inner dimension 120, etc.) to have as small of a selected outer diameter (e.g., as small as possible) while having (1) an increased ability to introduce and withdraw a guidewire within a lumen of the cannula (e.g., using less force), (2) an increased ability to inject fluoroscopic agent (e.g., using less injection pressure), (3) an increased ability to inflate the balloon at the distal portion of the catheter (e.g., using less inflation pressure), (4) a smaller required outer diameter introducer/guide catheter, and (5) fewer insertion site complications.

For instance, the design and manufacture of apparatus 100 may provide a large enough effective space between the outer diameter of apparatus 100 and the inner diameter of a guiding catheter that apparatus 100 may be disposed within (e.g., such as to be advanced within a blood vessel) to lower the resistance to fluid flow (e.g., with viscous radiopaque contrast) in the space, while at the same time maximizing the effective cross sectional area of the agent infusion lumen (e.g., of infusion tube 125) and the balloon inflation lumen (e.g., of inflation tube 140). Thus, the design and manufacture of apparatus 100 may produce a cannula or infusion catheter with a smaller outer diameter than other designs, so that apparatus 100 can be used with a smaller outer diameter guiding catheter to minimize post operative wound closure complications arising from punctured wound, typically in the femoral artery in the thigh.

Although discussed primarily in terms of embodiments having an inflation tube for inflating a balloon, in an alternative embodiment (not shown) the balloon (and accompanying inflation tube) are omitted.

Furthermore, it is considered that guidewire tube 130 and inflation tube 140 may be made from a single piece of tube (e.g., without any joined tube or tubing sections), extending from proximal end 104 to distal end 106 of apparatus 100. Alternatively, guidewire tube 130, infusion tube 125, and/or inflation tube 140 may be made with two or more joined sections of tube or tubing that do not leak or retard performance of apparatus 100 as an infusion catheter.

Figure 2:
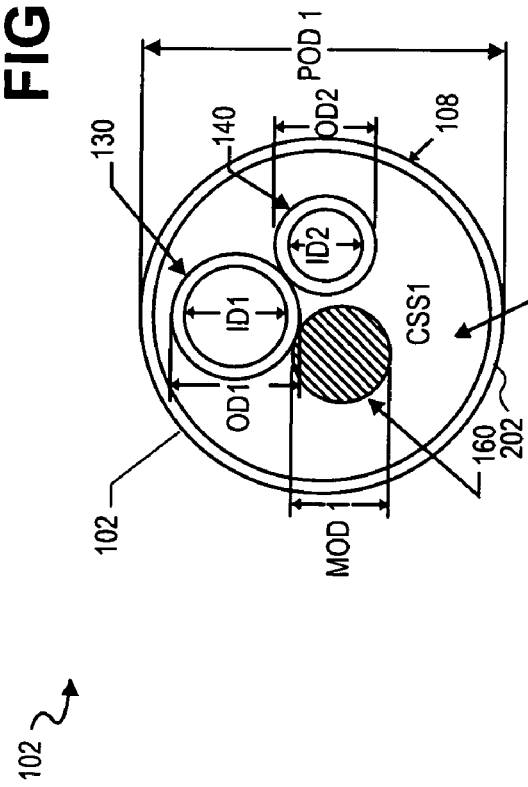
FIG. 2 shows a sectional side view of FIG. 1 through line A of FIG. 1.

FIG. 2 shows a sectional side view of FIG. 1 through line A of FIG. 1. FIG. 2 shows proximal cannula 102 having wall 202 enclosing inner dimension 120, inflation tube 140, guidewire tube 130, and cross-sectional area or size CSS1. Cross-sectional size CSS1 may be a cross-sectional area, cavity space, or volume defined between inner dimension 120 (e.g., such as the inner diameter or surface of wall 202), the outer dimension of guidewire tube 130, and the outer dimension of inflation tube 140. FIG. 2 also shows proximal cannula 102 having surface 108 and outer diameter POD1. Optionally, proximal cannula 102 may have support mandrel 160 having outer diameter MOD1. It is considered that the cross-sectional size CSS1, inner dimension 120, outer dimensions of inflation tube 140 and guidewire tube 130, and optionally outer diameter of support mandrel 160 may have sizes such that when a treatment agent is infused from proximal end 104 to distal end 106 of apparatus 100, the infusion resistance to infuse the treatment agent therebetween is reduced by between zero and one hundred percent, such as by 30 percent, 40 percent, 50 percent, 60 percent, or more. This reduction in infusion resistance may be attributable, at least in part, to the infusion resistance one obtains when proximal cannula 102 is constructed to contain inner dimension 120 as the infusion path, instead of an extension of infusion tube 125, for example. For instance, the pressure required to infuse a fluid from proximal end 104, through inner dimension 120 (optionally through lumen 124) and cannula 125 and out distal end 106 may be defined as the product of flow rate of the fluid and the infusion resistance.

In some cases, the infusion resistance can be further reduced by making proximal cannula 102 larger in inner diameter (and hence, larger in outer diameter). However, this design selection may be constrained by the size of a guide catheter to be used to guide apparatus 100. For instance, selection of the inner diameter of cannula 102 may include considering the difficulty (e.g., pressure required, flow rate, and/or infusion resistance) in injecting contrast media into the inner diameter of a guide catheter around apparatus 100, and out into the blood vessel to see if balloon 110 is sufficiently inflated to occlude the vessel (e.g., proximal portions of apparatus 100 may be inside the guide catheter at this time). If contrast is seen on fluoroscopy to go past the inflated balloon, then the vessel is not occluded. Specifically, design considerations reducing the outer diameter of proximal cannula 102 may include balancing the decrease in infusion resistance of the infusion path including inner dimension 120 against the increase in infusion resistance of the infusion of contrast flow into the guide catheter's inner diameter around the outer diameter of apparatus 100.

According to embodiments, diameter POD1 may be a diameter between 0.04 inches and 0.06 inches, such as by being a diameter of 0.04 inches, 0.0472, inches, 0.0475 inches, 0.0482 inches, 0.0492 inches, 0.0497 inches, 0.0499 inches, 0.052 inches, 0.055 inches, or 0.06 inches.

Wall 202 may include materials described above for apparatus 100. For example, appropriate materials for wall 202 include a thermoplastic, a polyetheretherketone (PEEK), a nylon (e.g., such as nylon 12, nylon 6,12), a polyethylene (PE) (e.g., such as a low density PE (LDPE), a medium density PE (MDPE) or a high density PE (HDPE), or a high durometer "Pebax"®, such as "Pebax"® 72D, a plastic, a polymer, a resin, a "Teflon"®, a block copolymer, a polycarbonate, a bio-compatible polymer, styrene, a urethane, an acetate, an acid, and/or an acrylate. FIG. 2 also shows inflation tube 140 having inner diameter ID2, and guidewire tube 130 having inner diameter ID1. Diameter ID1 may be a diameter between 0.01 inches and 0.035 inches, such as by being a diameter of 0.0145 inches, 0.0155 inches, 0.0165 inches, 0.0175 inches, 0.0185 inches, 0.0195 inches, 0.02 inches, 0.025 inches, 0.03 inches, and 0.035 inches. For peripheral vessel applications, ID1 may be 0.025 inches to allow 0.018 inches guidewire usage. Diameter ID2 may be a diameter similar to diameter ID1. FIG. 2 also shows inflation tube 140 having outer diameter OD2 and guidewire tube 130 having outer diameter OD1. Diameter OD1 may be a diameter of between 0.01 inches and 0.25 inches, such as by being a diameter of 0.0125 inches, 0.0155 inches, 0.0175 inches, 0.0185 inches, 0.0195 inches, 0.0215 inches, 0.0225 inches, 0.0235 inches, 0.025 inches, 0.03 inches, and 0.035 inches. In some designs, OD1 may be between 0.014 inches and 0.035 inches. It is considered that outer diameter OD1 may be a diameter similar to diameter OD2.

Support mandrel 160 may extend from proximal end 104 of proximal cannula 102 to distal end 106 of distal shaft 101. Moreover, support mandrel 160 may have a constant outer diameter (e.g., as shown in FIGS. 1-5), such as an outer diameter of less than 0.017 inches in diameter. Alternatively, support mandrel 160 may have an outer diameter at proximal end 104 of less than 0.17 inches in diameter and increment or reduce in diameter as support mandrel 160 extend toward distal end 106 to lesser outer diameters, until support mandrel 160 reaches a distal diameter of between 0.012 inches and 0.003 inches in diameter. Support mandrel 160 may be anchored at proximal adapter 150, proximal end 104, distal end 107, proximal end 105, balloon 110, band 170, distal end 106, and/or various other points within apparatus 100. For example, mandrel 160 may have outer diameter MOD1 of less than 0.017 inches in diameter that is constant from end 106 to band 170 at balloon section 111, where mandrel 160 may be anchored. In another instance, support mandrel 160 may have an outer diameter at proximal end 104 of less than 0.017 inches in diameter and increment or reduce in diameter as support mandrel 160 extend toward distal shaft 101 to lesser outer diameters, until support mandrel 160 reaches and is anchored at proximal end 105 of distal shaft 101. Also, mandrel 160 may have a diameter greater than 0.017 inches, such as a diameter of 0.025 inches to allow catheter designs for peripheral vessel applications.

Support mandrel 160 may be used to add stiffness to and/or reinforce apparatus 100, such as to prevent the apparatus from kinking. Support mandrel 160 may include one or more of titanium, nickel-titanium (NiTi), stainless steel, a plastic, a polymer, a resin, and/or a "Teflon"®, a polyether block amide resin having a durometer hardness of about 50 to about 70 shore D, a polyimide, a polyethylene, and/or other suitable materials or metals, such as those having a sufficient stiffness to prevent the apparatus 100 from kinking. Thus, support mandrel 160 may prevent the apparatus 100 from kinking when the apparatus is not supported by a guidewire (e.g., such as is guidewire 133 or a guidewire of a guide catheter). Moreover, according to embodiments, mandrel 160 may have various cross-sectional shapes, such as a circle, an oval, a square, a rectangle, a polygon, a curved cross-sectional shape, or a combination thereof, as mandrel 160 extends through apparatus 100.

In some embodiments, support mandrel 160 may be omitted entirely, run the entire length of the catheter (with a diameter that decreases with distance towards distal end 106), be mainly only in the distal shaft 101 or be mainly only in the proximal cannula, depending upon the design details, manufacturing process, and catheter material choices. For instance, support mandrel 160 may be eliminated entirely and its support functions may be assumed by distal shaft 101 (e.g., the material/dimension choices thereof) and/or a guidewire that distal shaft 101 may be engaged with in rapid exchange or over-the-wire designs of apparatus 100. Also, some embodiments are a version of apparatus 100 without support mandrel 160 or guidewire tube 130.

Figure 3:
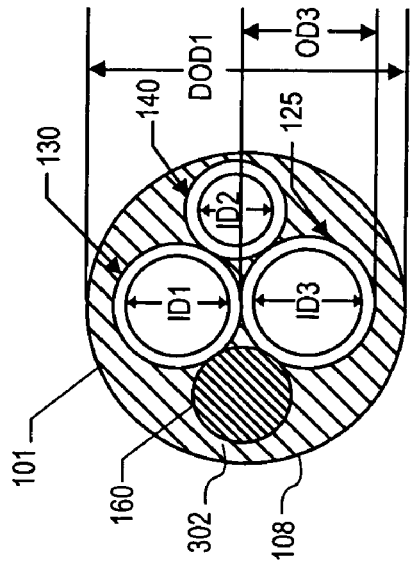
FIG. 3 shows a sectional view of FIG. 1 through line B of FIG. 1.

FIG. 3 shows a sectional view of FIG. 1 through line B of FIG. 1. FIG. 3 shows distal shaft 101 having outer diameter DOD1, surface 108, and material 302. Distal shaft 101 includes inflation tube 140, guidewire tube 130, and infusion tube 125. Infusion tube 125 is shown having inner diameter ID3 and outer diameter OD3. Inner diameter ID3 may be a diameter as described above for inner diameter ID2. Outer diameter OD3 may be an outer diameter as described above for OD2. Optionally, distal shaft 101 may include support mandrel 160, as described above.

Distal shaft 101 may have outer diameter DOD1 of between 0.025 inches and 0.06 inches, such as by having an outer diameter of 0.025 inches, 0.035 inches, 0.04 inches, 0.0475 inches, 0.05 inches, 0.052 inches, 0.054 inches, 0.056 inches, 0.058 inches, and 0.06 inches.

Infusion tube 125, guidewire tube 130, and inflation tube 140 may each include materials as described above for apparatus 100. Moreover, infusion tube 125, guidewire tube 130, and inflation tube 140 may each include one or more outer layers of a thermoplastic, a nylon and/or "Pebax"®, an adhesive polymer (e.g., such as "Primacore"™, Primacore™ is a Trademark of Dow Plastics), a lubricious inner layer of polyester, high density polyethylene (HDPE) or fluorinated ethylene-propylene (FEP), a plastic, a polymer, a resin, a "Teflon"®, a block copolymer, a polycarbonate, a bio-compatible polymer, styrene, a urethane, an acetate, an acid, and/or an acrylate. Specifically, infusion tube 125, guidewire tube 130, and inflation tube 140 may each include an outer layer of thermally bondable nylon and/or "Pebax"® formed over a layer of adhesive polymer (e.g., such as "Primacore"™, Primacore™ is a Trademark of Dow Plastics) formed over a lubricious inner layer of polyester, high density polyethylene (HDPE) or fluorinated ethylene-propylene (FEP).

Also, material 302 may include may each include materials as described above for apparatus 100. Specifically, material 302 may include one or more of a thermoplastic, a PEEK, a nylon (e.g., such as nylon 12, nylon 6,12), a polyethylene (PE) (e.g., such as a low density PE (LDPE), a medium density PE (MDPE) or a high density PE (HDPE), or a high durometer "Pebax"®, such as "Pebax"® 72D, a plastic, a polymer, a resin, a "Teflon"®, a block copolymer, a polycarbonate, a bio-compatible polymer, styrene, a urethane, an acetate, an acid, and/or an acrylate. For instance, material 302 may be formed into shaft 101 using a heat shrink process known in the art and/or described below for block 730. In some cases, material 302 may include a separate material put into place, shaped or formed over tube 130, tube 140, tube 125, and optionally mandrel 160, by heating a heat shrink tube disposed over the separate material. Specifically, shaft 101 may be formed by heating a heat shrink tube slid or disposed over a tube of nylon and/or "Pebax"® with an inner layer of adhesive polymer (e.g., such as "Primacor"™) formed around infusion tube 125, guidewire tube 130, and inflation tube 140. Thus, material 302 may be an outer material, layer, or surface of shaft 101 formed by a heat shrink process to create a solid shaft around or including infusion tube 125, guidewire tube 130, and inflation tube 140, while allowing those tubes (e.g., with our without mandrel disposed therein) to retain their inner dimension or inner cross-sectional area. As mentioned above, material 302 may also be formed over or around support mandrel 160. Alternatively, material 302 may include the material of tube 130, tube 140, and/or tube 125, put into place, shaped or formed into shaft 101 by heating a heat shrink tube disposed over tube 130, tube 140, and tube 125 (and optionally mandrel 160) without a separate outer material.

Figure 4:
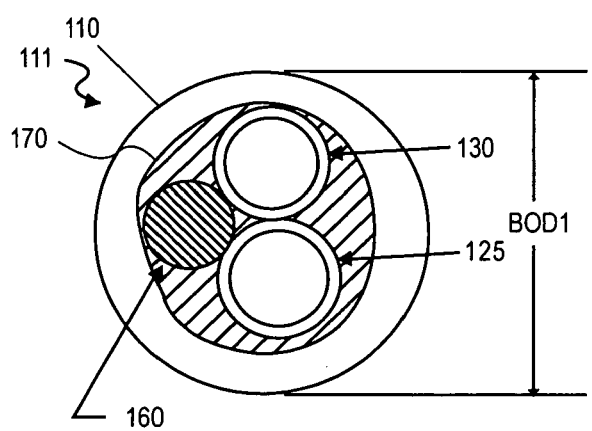
FIG. 4 shows a sectional view of FIG. 1 through line C of FIG. 1.

FIG. 4 shows a sectional side view of FIG. 1 through line C of FIG. 1. FIG. 1 shows balloon 110, guidewire tube 130, and infusion tube 125. Optionally, support mandrel 160 may be within balloon 110. Balloon 110 may be axially coupled to exterior surface 108 of distal shaft 101 at or adjacent distal end 106, as shown in FIG. 1. Thus, as shown in FIG. 4, the extension of distal shaft 101 through balloon 110 may have a reduced outer diameter when uninflated, such as diameter BOD1. Balloon 110 may have a property such that when inflated, balloon 110 will expand in size to an outer diameter sufficient to occlude a blood vessel.

Figure 5:
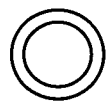
FIG. 5 shows a sectional view of FIG. 1 through line D of FIG. 1.
Figure 5:
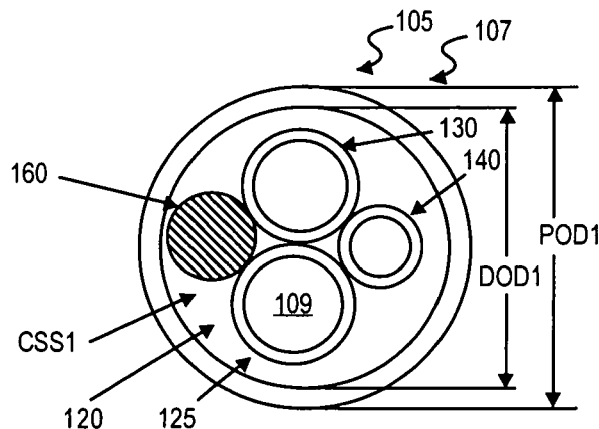

FIG. 5 shows a sectional side view of FIG. 1 through line D of FIG. 1. As shown in FIG. 5, inner dimension 120 of proximal cannula 102 extends over outer diameter DOD1 of distal shaft 101. Specifically, proximal end 105 of distal shaft 101 is under distal end 107 of proximal cannula 102, and may be attached thereto, such as by adhesive, heat-bonding, or laser bonding. FIG. 5 also shows guidewire tube 130, inflation tube 140, and infusion tube 125. In addition, FIG. 5 shows opening 109 formed between the inner dimension or inner diameter of infusion tube 125 and inner dimension 120. As mentioned above, support mandrel 160 may optionally exist in FIG. 5.

Moreover, according to embodiments, cannula 102, distal shaft 101, inner dimension 120, lumen 124, guidewire tube 130, inflation tube 140, and infusion tube 125 may have various cross-sectional shapes, such as a circle, an oval, a square, a rectangle, a polygon, a curve, or a combination thereof. Also, according to embodiments, lengths, diameters, materials, and other characteristics of cannula 102, distal shaft 101, inner dimension 120, lumen 124, guidewire tube 130, inflation tube 140, balloon 110, infusion tube 125, and other components mentioned above may be selected so that apparatus 100 may assist in or be used for treatment agent and/or cell infusion to treat acute myocardia infraction (AMI) or other forms of loss of heart function due to heart muscle damage.

Figure 6:
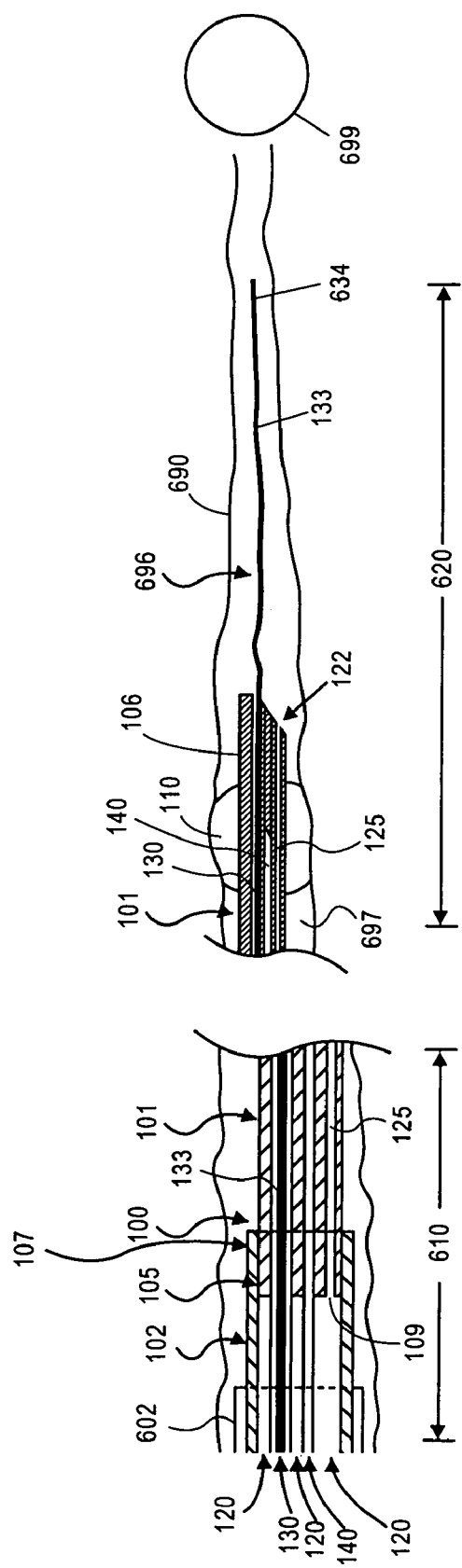
FIG. 6 schematically illustrates the placement of the apparatus of FIG. 1 in a blood vessel.

For example, FIG. 6 schematically illustrates the placement of apparatus 100 in a blood vessel. FIG. 6 shows proximal cannula 102 and the proximal portion of distal shaft 101 in first segment of blood vessel 610. FIG. 6 also shows the distal portion of distal shaft 101, balloon 110, distal end 106, and guidewire 133 in second segment of blood vessel 620. It is contemplated that first segment of blood vessel 610 and second segment of blood vessel 620 may be from a single or from more than one blood vessel. FIG. 6 shows balloon 110 inflated to occlude blood vessel 690 proximal to region of interest 696.

According to embodiments, apparatus 100 may be inserted into a guide catheter (e.g., such as guide catheter 602) and guided to a region of interest of a blood vessel (e.g., such as blood vessel 690). Then, apparatus 100 may be extended towards a treatment zone, such as region of interest 696 of blood vessel 690. Next, a sufficient volume and pressure of a treatment agent may be infused into inner dimension 120 (e.g., such as by being infused into proximal end 104 via lumen 124 and/or opening 152), through opening 109, and into fusion tube 125 (e.g., such as by being infused into and through inner dimension 120 and around the outer dimension of guidewire tube 130 and inflation tube 140 within inner dimension 120). Thus, a sufficient amount of treatment agent may be infused into apparatus 100 and exit infusion opening 122 to treat region of interest 696 of blood vessel 690 distal to occluding balloon 110.

Also, a guide catheter in which apparatus 100 may be inserted (e.g., guide catheter 602), may be selected to have an inner dimension suitable to receive apparatus 100 (e.g., an infusion catheter), so that when the guide catheter and apparatus 100 (e.g., the infusion catheter) are extended to a region of interest in a blood vessel and contrast is injected between the outer diameter of apparatus 100 and the inner diameter of the guide catheter, fluoroscopic imaging may successfully image to locate the distal end of the guide catheter. Specifically, guide catheter 602 may be selected having a guide catheter inner diameter or dimension sufficiently greater than outer diameter POD1 and outer diameter DOD1 to allow a sufficient volume of contrast to be injected through the space between diameter POD1, diameter DOD1, and the inner diameter or dimension of guide catheter 602 and out of a distal end of guide catheter 602 to image a vessel path or "roadmap". Hence, guide catheter 602 may be selected with an inner diameter, and apparatus 100 may be selected with outer diameter POD1 and outer diameter DOD1 to allow a volume of contrast to be injected into, infused into, or fill a length of a vessel or vessels distal to the distal end of guide catheter 602 to successfully perform fluoroscopic imaging of a vessel roadmap of the vessel or vessels.

Moreover, apparatus 100 may be extended past the distal end of guide catheter 602, such as shown and described with respect to FIG. 6. Specifically, distal shaft 101 and proximal cannula 102 may have a dimension, such as an outer diameter or dimension, suitable for percutaneous advancement through a blood vessel, such as blood vessel 690 (e.g., such as a vein or artery of a human being, including the veins and arteries of the human heart). Thus, it is contemplated that when apparatus 100 is extended beyond the distal end of guide catheter 602, and balloon 110 is inflated to occlude a blood vessel, such as blood vessel 690 proximate to region of interest 696, a volume of a contrast may be infused between the inner dimension of the guide catheter and the outer dimension of apparatus 100 (e.g., such as between an inner diameter of guide catheter 602 and outer diameter POD1 and outer diameter DOD1) and infused into a region of the blood vessel proximate to balloon 110, such as region 697, as shown in FIG. 6), where the volume of contrast infused is sufficient for successful viewing of the contrast at region 697 to determine whether blood vessel 690 is occluded by balloon 110. It is contemplated that blood and/or other fluids may flow in blood vessel 690 in a direction from proximal cannula 102 towards distal shaft 101 or in a reverse direction (e.g., such as depending on the advancement of apparatus 100 into the blood vessel, and whether the blood vessel is a vein or artery).

According to embodiments, the placement of apparatus 100 in a blood vessel, such as shown in FIG. 6, may be used to occlude a coronary artery at the former site of an Myocardial Infarction (MI), such as a blood clot in the coronary artery, or at a site feeding tissue affected by Chronic Heart Failure (CHF) during and after an injection of a bone marrow and/or a blood derived stem cell treatment agent. For instance, FIG. 6 also shows the distal portion of distal shaft 101, balloon 110, and distal end 106 proximal to distal vessel 45 branches leading to a capillary bed 699.

Thus, apparatus 100 may be used to inject various substances into various vessels (e.g., vessels branching off of vessel 690 distal to end 106 shown in FIG. 6) while balloon 110 is inflated and occluding or partially occluding vessel 690. In these cases, inflated balloon 110 helps ensure that the injected substance will better travel distal to apparatus 100/balloon 110 (e.g., into vessels branching from vessel 690, such as distal vessel branches leading to a capillary bed 699) and that the injected substance's travel proximal to apparatus 100/balloon 110 is stopped or inhibited. For instance, when balloon 110 is inflated, the blood flow in vessel 690 is stopped or inhibited; such that the injected material (e.g., exiting opening 122) resides in the affected vessel tree (e.g., vessels branching from vessel 690, such distal vessel branches leading to a capillary bed 699), the connected capillaries (e.g., capillaries lead to by distal vessel branches leading to a capillary bed 699), the tissues, and/or the organ (e.g., a heart) for a longer time than it would with a normal blood flow.

In coronary and other arteries (e.g., such as where vessel 690 is an artery), after injecting treatment agent (e.g., stem cells and/or bone marrow), balloon 110 may be kept inflated to stop blood flow (occlusion) for a period of time (e.g., about 3 minutes), so the treatment agent will not be rapidly washed through the affected capillary bed (e.g., a capillary bed lead to by distal vessel branches leading to a capillary bed 699) and out of the heart (or other organ/tissue). Alternatively, in coronary and other veins (e.g., such as where vessel 690 is a vein), inflated balloon 110 allows the injected treatment agent (e.g., bone marrow and/or stem cells) to force the blood to reverse its flow direction and for the treatment agent to be forced into an affected capillary bed under pressure (e.g., a capillary bed lead to by distal vessel branches leading to a capillary bed 699). Thus, the affected capillaries of a bed lead to by distal vessel branches leading to a capillary bed 699 are subjected to a higher than normal pressure and, if balloon 110 remains inflated after the injection, the flow forces (flowrate) in the affected capillaries can be reduced.

In either veins or arteries, it is possible to further direct the flow path of the treatment agent, by providing a further occlusion distal to balloon 110. For instance, another occlusion device or balloon may be attached to end 634 of guidewire 133 as shown in FIG. 6 so that treatment agent can be directed into another blood vessel(s) branching off of vessel 690 between balloon 110 and a balloon attached to end 634. The branch vessel(s) will then receive all or an increased portion of the treatment agent.

Figure 7:
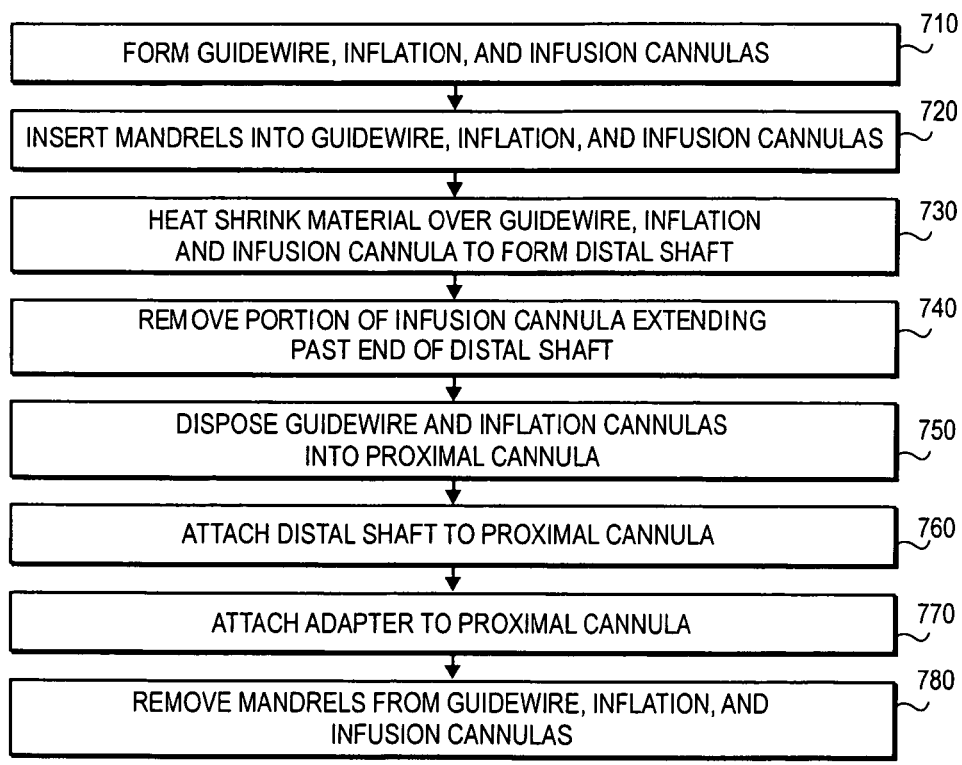
FIG. 7 is a flow diagram of a process for manufacturing an apparatus for infusing a treatment agent to a region of interest in a blood vessel.

FIG. 7 is a flow diagram of a process for making or manufacturing an apparatus for infusing a treatment agent to a region of interest in a blood vessel (e.g., such as apparatus 100). At block 710, a guidewire tube, an inflation tube, and an infusion tube are formed. For example, block 710 may describe forming inflation tube 140, guidewire tube 130, and infusion tube 125. Each tube may be formed by tri-layer extruding each tube with an outer layer of Pebax® or nylon formed over a layer of adhesive polymer (e.g., such as Primacor™) formed over an inner layer of polyester, high density polyethylene (HDPE) or fluorinated ethylene-propylene (FEP). It is contemplated that the layer of adhesive polymer may not be used in some cases, such as where the polymers (e.g., the inner layer polyester, HDPE or FEP and outer layer Pebax® and/or a nylon material) of the guidewire, infusion, or inflation tube are chosen to be miscible with each other or have their surface(s) etched, such that an adhesive polymer is not required between the inner and outer layers. It is also contemplated that the tubes may be formed by injection molding or rolling. According to embodiments, block 710 may include formation of proximal cannula 102, such as by extruding with PEEK.

Next, at block 720, mandrels are inserted into the guidewire tube, the inflation tube, and the infusion tube. Alternatively, it is considered that blocks 710 and 720 might include inserting mandrels into the tubes while or before forming the tubes, such as when the tubes are formed by dipping or rolling the mandrels in one or more heated or liquid materials which then dry on the mandrels to form the tubes.

At block 730, material is heat-shrunk over the guidewire tube, the inflation tube, and the infusion tube to form the distal shaft. For example, block 730 may correspond to forming distal shaft 101 by using a heat shrink process to form or shape material 302 over guidewire tube 130, inflation tube 140, and infusion tube 125. At block 730, the cannulas may or may not have mandrels disposed therein. Block 730 may include a length or portion of the guidewire tube and the inflation tube extending beyond one of the ends of the heat-shrunk material, or distal shaft formed. It is also considered that the infusion tube may extend past the end of the heat-shrunk material or distal shaft formed. Block 730 may correspond to using an outer layer of polyester, high density polyethylene (HDPE) or fluorinated ethylene-propylene (FEP) in a heat shrink process to form or shape a Pebax® and/or a nylon material (optionally having an inner layer of adhesive polymer (e.g., such as Primacor™)) around the infusion tube, the guidewire tube, and the inflation tube to form the distal shaft.

For instance, block 730 may include a heat shrink process as known in the art and/or described above for shaft 101. In some cases, block 730 may include a heat shrink process where a piece of heat shrink tube (e.g., polyester, HDPE or FEP) is placed over an assembly (e.g., guidewire, infusion, and inflation tube) and heated (usually by hot air), usually starting at an end of the assembly. The heat shrink tube or material thereof is chosen such that it will not bond or fuse with the assembly materials that it contacts and its shrink temperature is compatible with the assembly polymers' melt characteristics. As the heat shrink tube begins to shrink in response to its rise in temperature, it contacts the assembly, which then also begins to rise in temperature rapidly. The shrunk inner diameter of the heat shrink tube can be chosen to be slightly smaller than the outer diameter of the desired finished assembly (e.g., distal shaft 101). As the assembly begins to form or shape (e.g., such as by softening or "melting" the outer material of distal shaft 101, the guidewire tube, the infusion tube, and/or the inflation tube), the forces applied to the assembly by the heat shrink tube (as it continues to attempt to shrink) causes, at least, a portion of the heated portion of the assembly (e.g., the outer material of distal shaft 101, the guidewire tube, the infusion tube, and/or the inflation tube) to flow together inside the inner diameter of the heat shrink tube material, usually into a more rounded shape and forces air out of the assembly, thus filling any gaps in the assembly. The heated portion is moved along the assembly toward the other end of the assembly, until the desired portions of the assembly have been fused together. When the assembly is sufficiently cooled, the guidewire, infusion, and inflation tube's mandrels (which hold the tubes, hold the tube's inner diameters open and round, and help keep the formed assembly straight during the heat shrink process) and the heat shrink tube are removed.

In some examples, the guidewire, infusion, and inflation tubes with mandrels in them (and optionally, mandrel 160) are placed inside a tube (or cannula) of Pebax, nylon or a Pebax nylon blend (with or without the adhesive polymer inner layer) to create the assembly. This assembly is then subjected to the heat shrink process, such as by being placed inside a piece of heat shrink tube, heated, cooled, and having mandrels (except optional mandrel 160, if present) and the heat shrink tube removed).

In other embodiments, the outer tube (e.g., Pebax, nylon or a Pebax nylon blend) may be omitted when forming a distal shaft. Here, the material on the outer diameters of the guidewire, infusion, and inflation tubes is sufficient (e.g., in volume along the length of the shaft) to form (e.g., by having sufficient material to shape, "melt", flow, or otherwise form the distal shaft outer surface during heating. In such a case, if one of the guidewire, infusion, and inflation tubes is to have extra material to form a distal shaft (as compared to the others), the extra material may be in the material of the infusion tube (e.g., the material that makes up the infusion tube prior to heating may be thicker than the others). This allows the guidewire and inflation tubes to be smaller in outer diameter to help minimize the outer diameter of proximal cannula 102. Smaller shaft outer diameter's have many benefits in catheter use (i.e. improved guide contrast flow, smaller required introducer/fewer insertion site complications, etc.).

At block 730, the temperature and dwell time (time a particular portion of distal shaft 101 is subjected to heat) of the heat shrink process may be chosen such that inner layers (e.g., an inner HDPE layer) of the 3 tubes (e.g., guidewire, infusion, and inflation tube) do not flow to a significant extent. Thus the inner diameters of these 3 tubes retain the desired lubricous and pressure resistant properties (e.g., of the HDPE). Since the HDPE inner diameter of the 3 tubes is surrounded by a layer of Pebax (nylon and/or Pebax-nylon blends) and the HDPE and Pebax are not miscible (will not bond/fuse together), a very thin layer of an adhesive polymer may be extruded between the HDPE and Pebax of each of the 3 tubes to bond the HDPE and Pebax together and form stronger tubes and a stronger distal shaft.

For instance, at block 710 an adhesive polymer may be extruded between the HDPE and Pebax in a 3-layer co-extrusion process (e.g., an extrusion process where the adhesive polymer is extruded over the HDPE and the Pebax is extruded over the adhesive polymer). Thus, it is substantially the Pebax, nylon or Pebax-nylon blend cannula layer that flows. The adhesive polymer layer may be extruded too thin and bonded to the HDPE too well to flow appreciably from the heat.

Also, in some designs, to form a distal shaft, the polymers to form the outer surface of a guidewire, infusion, and inflation tube (e.g., the outer layer Pebax® and/or a nylon material) and/or the polymers to form a material around the guidewire, infusion, and inflation tubes may be chosen that are miscible with each other or have their surface(s) etched, such that an adhesive polymer is not required between the tubes and the surrounding material. For instance, the guidewire, infusion and inflation tubes can be made of an HDPE and low density polyethylene (LDPE) 2-layer co-extrusion; HDPE on the inner diameter and LDPE on the outer diameter. In another example, the inner diameter of the tubes could be a thin perfluorocarbon tube (i.e. PTFE, FEP) with its outer diameter etched and the outer diameter of the tubes could be a nylon, a Pebax or a Pebax-nylon blend. For instance, the proximal cannula could be made of an acetal, polyimide, HDPE, Medium Density Polyethylene (MDPE) or polyethylene terephthalate (PET). Other processes that could be used are, for example, multi-lumen extrusion and heated press molding.

It is also considered that block 710, 720, and/or 730 may include forming inflation tube 140, guidewire tube 130, and infusion tube 125, and/or distal shaft 101 by a multi-lumen extrusion process.

At block 740, a portion of the infusion tube extending past the end of the distal shaft is removed. For example, block 740 may correspond to removing a portion of infusion tube 125 extending distal to distal end 107 of distal shaft 101, such as is shown in FIG. 1. Thus, block 740 may include forming opening 109 between infusion tube 125 and inner dimension 120 when distal shaft 101 is attached to proximal cannula 102. The portion of infusion tube 125 may be removed by cutting, melting, crimping, or slicing where the termination is desired. In addition, block 740 may include removing portions of the tubes at the distal end of distal shaft 101, such as to form infusion opening 122 and guidewire opening 132 as shown in FIG. 1. Alternatively, block 740 may be skipped, such as in embodiments where infusion tube 125 already has a desired length and/or does not extend distal to distal end 107 of distal shaft 101.

At block 750, the guidewire tube and the inflation tube are disposed into proximal cannula 102. For example, guidewire tube 130 and inflation tube 140 may be disposed within inner dimension 120. Block 750 may include disposing inflation tube 140 and guidewire tube 130 into inner dimension 120 sufficiently to extend the cannulas from distal end 107 of proximal cannula 102 to proximal end 104. Moreover, the tubes may be extended beyond proximal end 104, such as for extension through adapter 150 to openings 153 and 154.

At block 760, distal shaft 101 is attached to proximal cannula 102. For example, block 760 may correspond to attaching proximal end 105 of distal shaft 101 to distal end 107 of proximal cannula 102 as described above with respect to FIGS. 1-5. Specifically, distal end 107 of proximal cannula 102 may extend over and be attached to proximal end 105 of distal shaft 101 by adhesive bonding, heat bonding, or laser bonding. Such bonding may include bonding by a heat shrink process (e.g., as known in the art and/or described above for block 730); by a process including a heat shrink tube; and/or by a process including an adhesive, a light, and/or a laser.

At block 770, an adapter, such as a three-way sidearm adapter, may be attached to the proximal cannula. For example, block 770 may correspond to attaching adapter 150 to proximal end 104 of proximal cannula 102, such as is described above with respect to FIG. 1. Thus, block 770 may include inserting a mandrel into opening 152, along length LL2 and into inner dimension 120 and infusing an adhesive into opening 152 and to inner dimension 120 to form lumen 124 as described above. Block 770 may also include removing that mandrel so that lumen 124 is formed.

Next at block 780, the mandrels may be removed from the guidewire tube, the inflation tube, and the infusion tube. Block 780 may correspond to removing mandrels from guidewire tube 130, inflation tube 140, and infusion tube 125. Block 780 may include removing mandrels via openings 152, 153, and 154 of adapter 150. Specifically, in one embodiment, a mandrel disposed within infusion tube 125 and lumen 124 may be removed by pulling it through opening 152 so that adhesive infused through opening 152 forms lumen 124.

According to embodiments, the blocks and processes thereof described above with respect to FIG. 7 may be performed in various orders, with additional processes therebetween, and without processes for certain blocks described above. For example, the process of FIG. 7 may be performed without blocks 720, 730, 750, and 780. In another embodiment, the order of block 770 and 780 may be switched, so that block 780 occurs prior to block 770. Moreover, block 770 may be performed before or after any other block of FIG. 7.

In some embodiments, a process for making or manufacturing an apparatus for infusing a treatment agent to a region of interest in a blood vessel (e.g., such as apparatus 100) may include the following. Make a distal portion of the apparatus (e.g., distal shaft 101) by (1) insert a mandrel (e.g., about 160 cm long) into a guidewire lumen tube (e.g., guidewire tube 130 that is about 130 cm long), (2) insert a mandrel (e.g., about 160 cm long) into an inflation lumen tube (e.g., inflation tube 140 that is about 130 cm long), and (3) insert a mandrel (e.g., about 160 cm long) into the infusion lumen (e.g., infusion tube 125 that is about 40 cm long). Inserting the three mandrels may include processes described above for block 720.

Then, insert these assemblies inside a distal outer member tube (e.g., distal shaft 101). Next, use heat shrink tube heat fuse the distal lumens (e.g., guidewire tube 130, inflation tube 140, and infusion tube 125) into the distal outer member tube. Inserting the assemblies and fusing may include processes described above for block 730.

The distal assembly (e.g., distal shaft 101) may then be slid inside a proximal shaft tube (e.g., proximal cannula 102 made of PEEK) then join the distal assembly with the proximal shaft tube, using adhesive. Sliding the distal assembly may include processes described above for block 750, and joining may include processes described above for block 760.

Now, align the distal end of the inflation lumen tube (e.g., inflation tube 140) near the proximal end of the balloon (e.g., balloon 110). Insert the distal shaft (e.g., distal shaft 101) into the proximal end of the balloon and laser seal the proximal end (e.g., seal proximal end of balloon 110 to distal shaft 101). Then, laser seal distal end of the balloon with the guidewire lumen tube and the infusion lumen tube (e.g., seal distal end of balloon 110 with guidewire tube 130 and infusion tube 125).

Here, all the mandrels may be removed from the assembly (e.g., removed from guidewire tube 130, inflation tube 140, and infusion tube 125). Removing may include processes described above for block 780.

Then, load two mandrels (e.g., about 40 cm long) into the proximal end of the guidewire and inflation lumens (e.g., into guidewire tube 130 and inflation tube 140). Now, slide the proximal ends of the guidewire lumen tube mandrel and the inflation lumen tube mandrel to the appropriate openings in a three way side arm (e.g., adapter 150). Insert a Teflon beading (e.g., about 5 cm long) into the infusion port of the side arm and inside of proximal shaft tube (e.g., inside proximal cannula 102 made of PEEK) and outside of the guidewire lumen tube and the inflation lumen tube (e.g., outside guidewire tube 130 and inflation tube 140).

Inject adhesive (e.g., ultraviolet (UV) curable adhesive) into the appropriate ports of the side arm (e.g., adapter 150) so that (1) the proximal shaft tube (e.g., inside proximal cannula 102 made of PEEK) proximal outer member is intimately bonded (e.g., chemically or atomically fused, bonded, or miscible) to the side arm, (2) the guidewire lumen tube (e.g., guidewire tube 130) is intimately bonded to the side arm, (3) the inflation lumen tube (e.g., inflation tube 140) is intimately bonded to the side arm, and (4) the Teflon beading creates a separate infusion channel (e.g., infusion lumen 124) to the space created between the proximal shaft tube and outside of the guidewire lumen tube and the inflation lumen tube (e.g., inner dimension 120 between inside of proximal cannula 102 and outside guidewire tube 130 and inflation tube 140). Finally, cure the adhesive and remove the mandrels (e.g., about 40 cm long mandrels) from the guidewire lumen tube and the inflation lumen tube (e.g., from guidewire tube 130 and inflation tube 140). Note that loading, sliding the proximal ends, inserting a beading, injecting, and curing may include processes described above for block 770. Also, removing may include processes described above for block 780.

In the foregoing specification, specific embodiments are described. However, various modifications and changes may be made thereto without departing from the broader spirit and scope of embodiments as set forth in the claims. The specification and drawings are, accordingly, to be regarded in an illustrative rather than a restrictive sense.

What is claimed is:

1. A catheter, comprising:
   a) an elongated shaft having a proximal shaft section, a distal shaft section, an infusion lumen, an inflation tube defining an inflation lumen, and a guidewire tube defining a guidewire lumen;

b) a balloon on the distal shaft section having an inflatable interior in fluid communication with the inflation lumen;

c) the proximal shaft section comprising an outer tubular member defining a proximal portion of the infusion lumen, and having a proximal portion of the guidewire tube extending in the infusion lumen and a proximal portion of the inflation tube extending in the infusion lumen;

d) the distal shaft section comprising a distal portion of the guidewire tube, a distal portion of the inflation tube, and an infusion tube defining a distal portion of the infusion lumen in fluid communication with the infusion lumen proximal portion, the inflation, guidewire, and infusion tubes having outer surfaces secured together along the distal shaft section; and e) a junction formed at a bond between a distal end of the proximal shaft section and a proximal end of the distal shaft section, the junction comprising the guidewire tube and inflation tube transitioning from being located within the infusion lumen of the proximal shaft section, to being located within the distal shaft section external to the infusion tube.

2. The apparatus of claim 1, wherein the infusion tube extends to a distal infusion port located distal to the inflatable interior of the balloon.

3. The apparatus of claim 1, wherein the guidewire tube extends to a guidewire distal port located distal to the inflatable interior of the balloon.

4. The apparatus of claim 1, wherein the outer surfaces of the inflation, guidewire, and infusion tubes are secured together with one of Pebax, Nylon, Pebax Nylon blend, and adhesive polymer inner layer.

5. The apparatus of claim 1, wherein the inflation tube comprises a proximal portion, and a distal portion having a higher flexibility than the proximal portion.

6. The apparatus of claim 1, wherein the guidewire tube comprises a single, one-piece tube.

7. The apparatus of claim 1, wherein the distal shaft section comprises an extruded tube having multiple lumens extruded therein forming a distal portion of the guidewire lumen in fluid communication with the guidewire tube, a distal portion of the inflation lumen in fluid communication with the inflation tube, and a distal portion of the infusion lumen in fluid communication with the infusion lumen proximal portion.

8. The apparatus of claim 1, wherein the proximal shaft section has a length between 100 centimeters and 130 centimeters, and an inner diameter between 0.0472 inches and 0.052 inches; the distal shaft section has a length between 20 millimeters and 40 millimeters, and an outer diameter of less than 0.052 inches; and the guidewire tube and the infusion tube have an inner diameter between 0.0155 inches and 0.0185 inches, and an outer diameter of between 0.0125 inches and 0.0235 inches.

9. The apparatus of claim 1, wherein the infusion tube, guidewire tube, and inflation tube each comprise an outer layer of a Pebax or a nylon formed over a layer of adhesive polymer formed over an inner layer of high density polyethylene; and wherein the proximal shaft section comprises polyetheretherketone (PEEK); and wherein the proximal shaft section comprises polyetheretherketone (PEEK); and wherein the distal shaft section includes a layer of one of a Pebax, a nylon, aPebax nylon blend, and an adhesive polymer inner layer formed around the infusion tube, guidewire tube, and inflation tube by a heat shrink process; and wherein the distal end of the proximal shaft section is attached to the proximal end of the distal shaft section with adhesive.

10. The catheter of claim 1, wherein the outer tubular member has an inner surface defining an outer surface of the proximal portion of the infusion lumen.

11. The apparatus of claim 1, wherein the outer surfaces of the inflation and infusion lumens are spaced apart and separated by the guidewire lumen along at least a section of the proximal shaft section.

12. The apparatus of claim 11, wherein the inflation and guidewire lumens extend side-by-side along the length of the proximal shaft section.

13. The apparatus of claim 1, further comprising an adapter attached to the proximal end of the proximal shaft section, the adapter including a guidewire opening for receiving a guidewire to be extended through the guidewire tube, and inflation opening having a dimension suitable for receiving fluid to be pushed into an occlusion balloon attached to the exterior surface of the distal shaft section, and an infusion tube extending from the infusion opening past the proximal end of the proximal shaft section and into the inner dimension.

14. The apparatus of claim 13, wherein the adapter is formed of molded plastic, and the infusion tube is formed of hardened adhesive, hardened resin, or molded plastic.

15. A catheter comprising:

a) an elongated shaft having a proximal shaft section, a distal shaft section, an infusion lumen, an inflation tube defining an inflation lumen, and a guidewire tube defining a guidewire lumen;

b) a balloon on the distal shaft section having an inflatable interior in fluid communication with the inflation lumen;

c) the proximal shaft section comprising an outer tubular member defining a proximal portion of the infusion lumen, and having a proximal portion of the guidewire tube extending in the infusion lumen and a proximal portion of the inflation tube extending in the infusion lumen; and d) the distal shaft section comprising a distal portion of the guidewire tube, a distal portion of the inflation tube, and an infusion tube defining a distal portion of the infusion lumen in fluid communication with the infusion lumen proximal portion, the inflation, guidewire, and infusion tubes having outer surfaces secured together along the distal shaft section, wherein an inflation tube proximal portion is formed of a different material than an inflation tube distal portion, and a distal end of the proximal shift is fusion bonded or adhesively bonded to a proximal end of the distal shaft to form a junction.

16. The apparatus of claim 15, wherein the distal end of the outer tubular member is fusion or adhesively bonded to an outer surface of the distal shaft section, and the inflation tube opening is radially aligned with the distal end opening of the outer tubular member.

17. A catheter comprising:

a) an elongated shaft having a proximal shaft section, a distal shaft section, an infusion lumen, an inflation tube defining an inflation lumen, and a guidewire tube defining a guidewire lumen;

b) a balloon on the distal shaft section having an inflatable interior in fluid communication with the inflation lumen;

c) the proximal shaft section comprising an outer tubular member defining a proximal portion of the infusion lumen, and having a proximal portion of the guidewire tube extending in the infusion lumen and a proximal portion of the inflation tube extending in the infusion lumen; and d) the distal shaft section comprising a distal portion of the guidewire tube, a distal portion of the inflation tube, and an infusion tube defining a distal portion of the infusion lumen in fluid communication with the infusion lumen proximal portion, the inflation, guidewire, and infusion tubes having outer surfaces secured together along the distal shaft section, further comprising a support mandrel extending within the proximal shaft section, within the distal shaft section and distal to the balloon.

18. The apparatus of claim 17, wherein the support mandrel is anchored to at least one of a proximal adapter at the proximal end of the proximal shaft section and the proximal end of the distal shaft section.

* * * * *